United States Patent
Blasche et al.

(10) Patent No.: US 6,460,206 B1
(45) Date of Patent: Oct. 8, 2002

(54) MEDICAL DIAGNOSTIC IMAGING APPARATUS

(75) Inventors: Mathias Blasche, Buckenhof; Matthias Drobnitzky, Spardorf, both of (DE)

(73) Assignee: Siemens Aktiengesellschaft, Munich (DE)

( * ) Notice: Subject to any disclaimer, the term of this patent is extended or adjusted under 35 U.S.C. 154(b) by 89 days.

(21) Appl. No.: 09/676,455

(22) Filed: Sep. 29, 2000

(30) Foreign Application Priority Data

Oct. 1, 1999 (DE) .......................................... 199 47 328

(51) Int. Cl.[7] .............................. B61B 6/02; A47B 13/00
(52) U.S. Cl. .............................. 5/601; 378/20; 378/209; 600/415
(58) Field of Search ................................ 5/601; 378/20, 378/209; 600/410, 415, 425

(56) References Cited

U.S. PATENT DOCUMENTS

| | | | |
|---|---|---|---|
| 4,117,337 A | | 9/1978 | Staats |
| 4,984,774 A | * | 1/1991 | Zupancic et al. ............ 254/122 |
| 5,199,123 A | * | 4/1993 | Jacques et al. ............. 378/209 |
| 5,272,776 A | * | 12/1993 | Kitamura ....................... 5/600 |
| 5,533,082 A | | 7/1996 | Grönemeyer et al. |
| 5,825,843 A | * | 10/1998 | Kobayashi ................... 378/20 |
| 6,138,302 A | * | 10/2000 | Sashin et al. ................... 5/600 |
| 6,259,942 B1 | * | 7/2001 | Westermann et al. ....... 378/162 |
| 6,269,501 B1 | * | 8/2001 | Li et al. ....................... 378/20 |

FOREIGN PATENT DOCUMENTS

| | | |
|---|---|---|
| DE | 195 08 715 | 9/1996 |
| DE | 195 20 017 | 11/1996 |

* cited by examiner

Primary Examiner—Michael F. Trettel
(74) Attorney, Agent, or Firm—Schiff Hardin & Waite

(57) ABSTRACT

A medical diagnostic imaging apparatus has a support device for the displacement of an examination subject positioned thereon in at least one displacement direction, a control device for the control of the displacements of the support device, an actuation device that is encompassed by the support device, that is oblong with reference to the displacement direction and that is actuatable at points at least in the displacement direction; and a setting device that encompasses the actuation device and that is connected to the control device for positioning a prescribable region to be imaged in the examination subject in an imaging volume of the apparatus on the basis of a displacement of the bearing device. The region to be imaged can be prescribed by an actuation of the actuation device at one of the points, whose position with respect to the oblong actuation device corresponds to a position of the region to be imaged within the examination subject in the displacement direction.

11 Claims, 2 Drawing Sheets

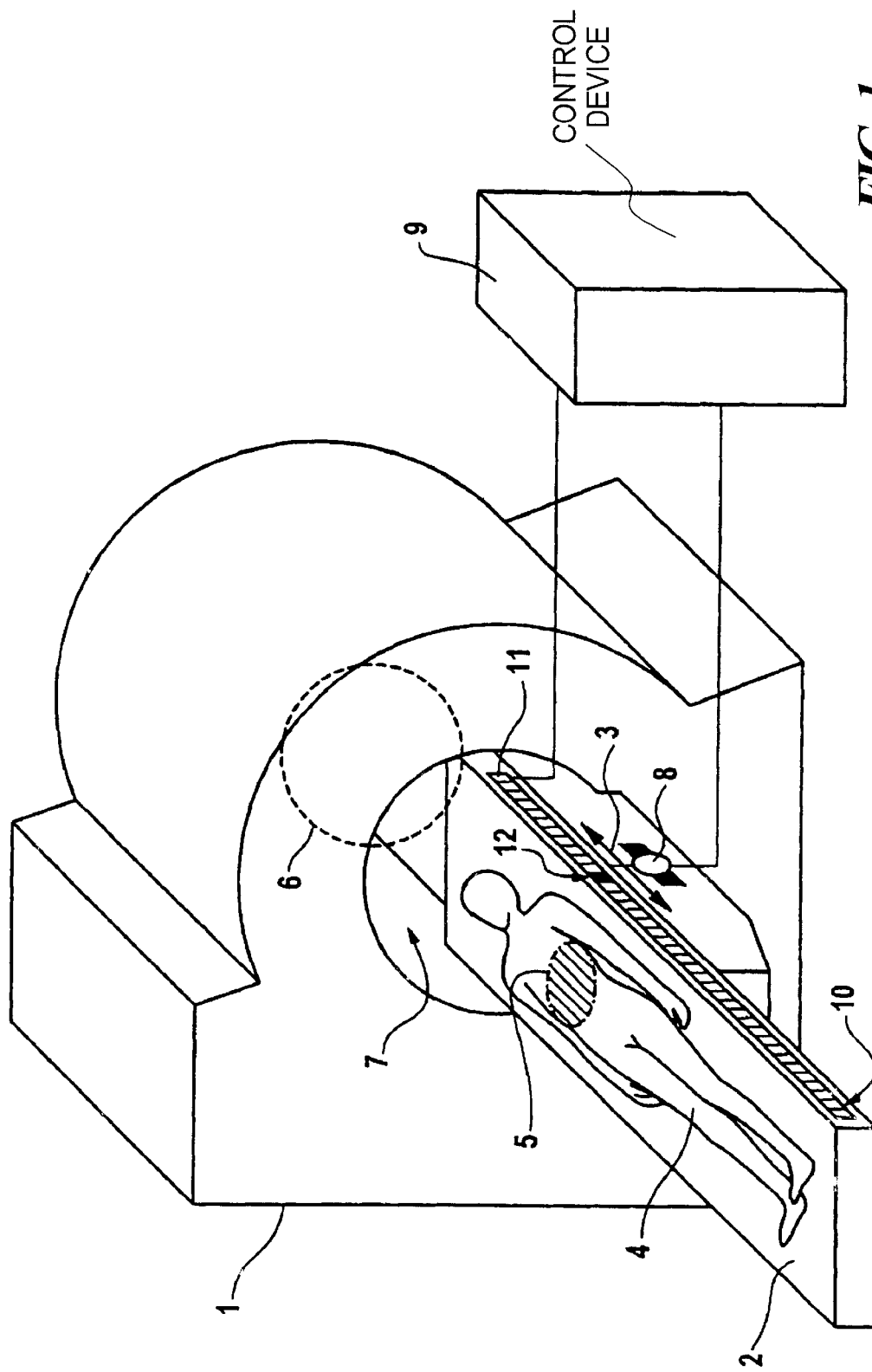

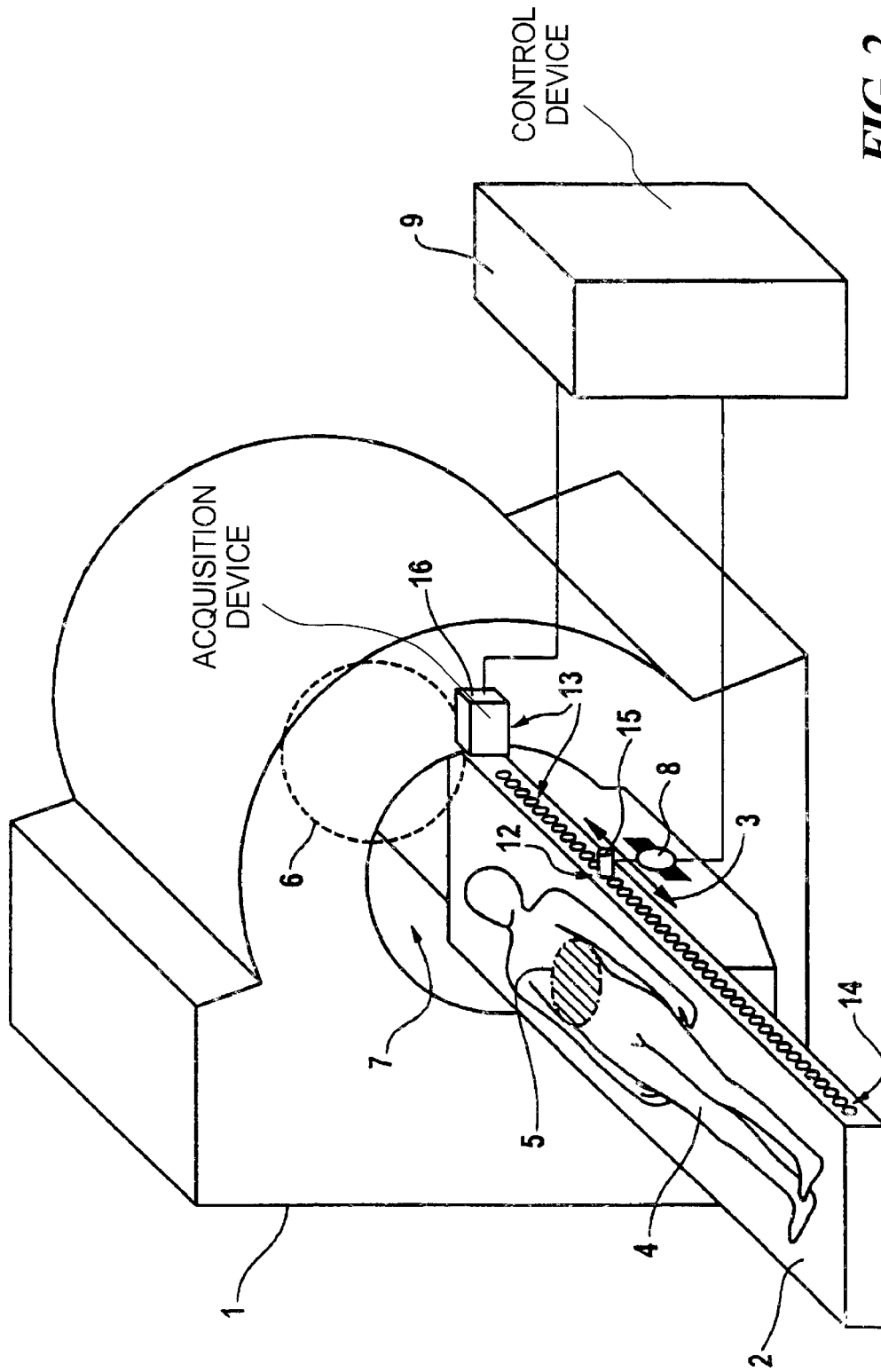

MEDICAL DIAGNOSTIC IMAGING APPARATUS

BACKGROUND OF THE INVENTION

1. Field of the Invention

The present invention is directed to an medical diagnostic imaging apparatus.

2. Description of the Prior Art

In medical diagnostic imaging apparatus, for example, computed or magnetic resonance tomography device, a region to be imaged in an examination subject is positioned in an imaging volume of the apparatus for producing images of this region. Particularly in a magnetic resonance tomography apparatus, wherein the imaging volume within an examination space is often surrounded by a closed housing except for an entry opening, positioning of the subject occurs with the assistance of a support device that is displaceable in at least one direction on which the examination subject is positioned. For example, a projector that projects an optical mark onto the examination subject, for example a patient, is situated in the region of the entry opening. Given an initial displacement event of the support device, the support device including the patient positioned thereon is initially controlled such that the optical marking on the surface of the patient marks a center of the region to be imaged. A remaining displacement distance of the support device into the imaging volume then derives from the known distance of the optical mark from the imaging volume. For definition of the center of the region to be imaged, the support device must be moved, possibly back and forth, until the optical mark hits the desired center. Since, moreover, the support device exhibits a comparatively low displacement speed, the aforementioned positioning procedure is comparatively time-consuming. For a computed tomography apparatus, a comparable positioning device is disclosed, for example, in U.S. Pat. No. 4,117,337.

Compared to the aforementioned positioning, German German OS 195 08 715 discloses a method and an apparatus for positioning a patient in a medical diagnostic imaging apparatus, wherein by the positioning sequences more dependably and faster. To that end, the region to be imaged is identified with a mark fixed to the patient. An image pick-up device outside the examination space, for example a video camera, acquires the mark fixed to the patient in an image. An image processing unit recognizes the mark in the image and determines the spatial position thereof. A control device determines a displacement path of the support device from the spatial position of the mark as well as from the known position of the imaging volume. The control device controls a corresponding movement of the support device along the aforementioned displacement path.

It is especially disadvantageous in the aforementioned apparatus that a complicated and expensive system containing an image pick-up device and an image processing unit with corresponding image recognition software is utilized. Further, the mark may possibly adhere differently as a consequence of different surface qualities of clothing or the skin of the patient, and a slippage of the mark is therefore possible. Moreover, an application of the mark, particularly on the face of the patient, is considered unpleasant by the patient.

SUMMARY OF THE INVENTION

It is an object of the present invention to provide a medical diagnostic imaging apparatus that allows a fast positioning and diminishes the aforementioned disadvantages of the prior art.

This object is inventively achieved by an imaging medical diagnosis apparatus that contains the following features: a support device for displacing an examination subject positioned thereon in at least one displacement direction; a control device for controlling the displacement of the support device; an actuation arrangement that is encompassed by the support device that is oblong with its longer dimension disposed in the displacement direction, and that is actuatable at points at least in displacement direction; and a setting device that interacts with the actuation device and that is connected to the control device for the positioning a prescribable region to be imaged in the examination subject in an imaging volume of the device by a displacement of the support device. The region to be imaged can be prescribed by an actuation of the actuation device at one of the points, the position thereof with respect to the oblong actuation device corresponding to the position of the region to be imaged within the examination subject in displacement direction.

After the examination subject has been placed onto the support device, the region to be imaged can be simply, intuitively and quickly prescribed by a person participating in the implementation of the diagnosis by actuating the actuation device at a point lying next to the region to be imaged, a following positioning event can be implemented fast and free of interruptions. The initially described, time-consuming positioning procedure upon employment of an optical projection is thus eliminated. Further, no marking needs to be applied to the examination subject for prescribing the region to be imaged. Moreover, the setting device is simple compared to an image processing unit and corresponding image recognition software, and thus can be economically implemented.

In an embodiment, the actuation device is arranged such that it is free from being covered by the examination subject. As a result, the actuation device can be actuated with free accessibly by the person participating in the implementation of the diagnosis without the examination subject having to be moved for this purpose.

In another embodiment, the actuation device has a spacial extent approximating the length of the examination subject along the displacement direction. As a result, any region to be imaged in the examination subject can be prescribed. No limitations as to sub-regions of the examination subject thus exist due to the actuation device.

In a further embodiment, the prescription device is fashioned such that positioning-relevant data are available with an actuation of the actuation device. As a result thereof, the positioning-relevant data are available immediately upon actuation, for example, at a higher-ranking control device, so that the control device is able, before the initial displacement to pre-calculate quantities relevant to the implementation of the diagnosis, taking the positioning-relevant data into consideration.

To that end, the actuation device can have a sensor field.

In a further embodiment, the actuation device is fashioned such that a marking is attachable to the points. As a result, the predetermined region to be imaged remains marked in visible fashion or for the person at the support device participating in the management of the diagnosis, so that a slippage of the examination subject, and thus of the predetermined region to be imaged, for example as a result of movements on the part of the examination subject, can be easily recognized.

In another embodiment, the setting device has an acquisition unit that is arranged at a part of the apparatus that is not displaceable together with the support device and is fashioned such that, given an initial displacement of the bearing device, a passage of the marking is acquired by the acquisition device and positioning-relevant data are available. As a result, the actuation device can be implemented as an exclusively mechanical or passive device, so that it needs no electrical energy supply.

In a further embodiment, the acquisition device and the marking are fashioned such that the acquisition device mechanically or optically acquires the passage of the marking. The mechanical or optical acquisition thereby guarantees a reliable acquisition in a simple way, even in an electromagnetically rugged environment as represented, for example, by the high static basic-magnetic field of a magnetic resonance tomography apparatus.

In another embodiment, the medical diagnostic imaging apparatus is a computed or magnetic resonance tomography apparatus. In particular, computed and magnetic resonance tomography apparatuses represent medical diagnostic apparatuses having a considerable acquisition cost, so that the aim is to operate such devices with an optimally high usage. An increase in the usage is achieved, for example, by shortening the examination time per patient is. As a result of the setting device, the positioning event per patient is shortened by about half a minute up to an entire minute, so that one to two additional patients can be examined per day. The term "computed tomography apparatus" encompasses x-ray and electron beam computed tomography apparatus as well as positron emission tomography apparatuses.

DESCRIPTION OF THE DRAWINGS

FIG. 1 is a perspective view of a magnetic resonance tomography apparatus having an actuation device in accordance with the invention.

FIG. 2 is a perspective view of a magnetic resonance tomography apparatus having an actuation and acquisition device in accordance with the invention.

DESCRIPTION OF THE PREFERRED EMBODIMENTS

As one embodiment of the invention, FIG. 1 shows a magnetic resonance tomography apparatus 1 as a medical diagnostic imaging apparatus in a perspective view. The magnetic resonance tomography apparatus 1 has a support device 2 that is displaceable in a displacement direction 3 on which an examination subject is positioned. In FIG. 1, the examination subject is a patient 4. The displaceable support mechanism 2 together with the patient 4 can be brought into various positions by a drive mechanism 8 in the non-displaceable part of the apparatus 1. The drive mechanism 8 is controlled by a control unit 9. For generating magnetic resonance images of a prescribable region 5 to be imaged in the patient 4, a region of the torso in the illustrated example, a center of the region 5 to be imaged is to be positioned or centered, in an imaging volume 6 within an examination space 7 of the apparatus 1 by displacing the support mechanism 2 together with the patient 4.

The magnetic resonance tomography apparatus 1 has a setting device 10 for prescribing the center of the region 5 to be imaged. The setting device 10 is connected to the control unit 9. An actuation device in an embodiment as a sensor field 11 is a component of the setting device 10. The support device 2 thereby laterally carries the sensor field 11. Due to the lateral arrangement of the sensor field 11, coverage by the patient 4 is prevented. After the patient 4 has been placed on the support device 2, a person participating in the implementation of the diagnosis preferably prescribes the middle of the region 5 to be imaged in the displacement direction 3 by actuating the sensor field 11 at a corresponding point 12, for example, next to the region 5 to be imaged. The support mechanism 2 is thereby in an initial position wherein, for example, it is withdrawn as far as possible from the examination space 7, so that the patient 4 can simply lie down on the support mechanism 2 or can be placed thereon. The aforementioned setting of the region 5 to be imaged is very simple and intuitive. Positioning-relevant data are present in the control unit 9 with the actuation of the sensor field 11. On the basis of these data as well as the known initial position of the support device 2, the control unit 9 calculates a displacement path that is necessary for centering the middle of the region 5 to be imaged in the imaging volume 6 of the apparatus 1. After a corresponding start signal, the control unit 9 controls an interruption-free displacement of the support device 2 along the aforementioned displacement path.

In the illustrated example of FIG. 1, the support device 2 is displaceable in only one spatial direction 3, so that a centering is only possible in one spatial direction 3 as a result of the displacement of the support device 2. In medical diagnostic imaging apparatuses having a support device that is displaceable in two or three spatial directions, the setting device is correspondingly expanded for prescribing the region to be imaged. To that end, for example, a number of sensor fields which is the same as a number of displacement directions are used.

As a further embodiment of the invention, FIG. 2 shows a perspective view of a medical diagnostic imaging apparatus having a setting device 13 that has an actuation device 14 and an acquisition device 16. As in FIG. 1, a magnetic resonance tomography apparatus 1 is shown as diagnostic apparatus. Compared to FIG. 1, the apparatus 1 has no sensor field 11; instead, it has an actuation device 14 that is fashioned such that a marking 15 can be attached to the corresponding point 12. Compared to FIG. 1, further, the apparatus 1 has an acquisition device 16 that is arranged at the non-displaceable part of the apparatus 1. The acquisition device 16, as a component of the setting device 13, is connected to the control unit 9 and is fashioned such that a passage of the mark 15 during an initial displacement of the support device 2 is acquired and reported to the control unit 9.

After the patient 4 has been placed onto the support device 2, the person participating in the implementation of the diagnosis prescribes the region 5 to be imaged by actuating the actuation device 14 at the corresponding point 12 by setting a marking 15. A marking 15 that can be optically or mechanically acquired by the acquisition device 16 is attached to the actuation device 14 at the corresponding point 12. To this end, the actuation device 14 is fashioned, for example, as a ledge having a number of holes, the holes serving as plug-in locations for the marking 15, for example, a marking pin.

During the initial displacement of the support device 2, the marking 15 passes the acquisition device 16 and is thereby acquired. The passage is reported to the control unit 9, whereupon the control unit 9 controls a further, permanently prescribed displacement path, so that the predetermined middle of the region 5 to be imaged is centered in the imaging volume 6 of the apparatus 1. The initial displacement is thereby carried out without interruptions.

In other embodiments, the acquisition of the marking 15 by the acquisition means 16 ensues based on electrical, magnetic or sonar principles. The markings 15 as well as the acquisition devices 16 must be compatible with magnetic resonance in all embodiments. This, in particular, means that the acquisition must also work dependably given a high-static basic magnetic field, given rapidly switched magnetic gradient fields and given radio-frequency transmission fields for the excitation of the magnetic resonance. Conversely, the acquisition device cannot disturb the operation of the magnetic resonance tomography apparatus.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical diagnostic imaging apparatus comprising:

an image data acquisition system having an imaging volume;

a support device adapted to receive an examination subject for displacing said examination subject along at least one displacement direction through said imaging volume;

a control device connected to said support device for controlling displacement of said support device;

an actuation device carried on said support device, said actuation device being oblong and having a longest dimension along said displacement direction, said actuation device having a plurality of points proceeding along said displacement direction at which said actuation device is respectively actuatable; and a setting device connected to said control device which interacts with said actuation device to set a prescribable region to be imaged within said examination subject in said imaging volume by displacement of said support device, said setting prescribing said region to be imaged by actuation of said actuation device at one of said points at a position within said oblong actuation device corresponding to the position of said region to be imaged along said displacement direction.

2. A medical diagnostic imaging apparatus as claimed in claim 1 wherein said actuation device is carried on said support device so as to be free from coverage by said examination subject.

3. A medical diagnostic imaging apparatus as claimed in claim 1 wherein said actuation device has a spatial extent along said displacement direction approximately equal to a length of said examination subject.

4. A medical diagnostic imaging apparatus as claimed in claim 1 wherein said setting device makes positioning-relevant data available upon actuation of said actuation device.

5. A medical diagnostic imaging apparatus as claimed in claim 1 wherein said actuation device contains a sensor field.

6. A medical diagnostic imaging apparatus as claimed in claim 1 wherein said actuation device includes a marking removably attachable at the respective points.

7. A medical diagnostic imaging apparatus as claimed in claim 6 comprising a component which is not displaceable with said support device, and wherein said setting device includes a detector device disposed at said component for detecting passing of said marking on an initial displacement of said support device, and wherein said setting device generates position-relevant data corresponding to the passing said marking.

8. A medical diagnostic imaging apparatus as claimed in claim 7 wherein said detection device mechanically detects passing of said marking.

9. A medical diagnostic imaging apparatus as claimed in claim 7 wherein said detection device optically detects passing of said marking.

10. A medical diagnostic imaging apparatus as claimed in claim 1 wherein said image data acquisition system is a computed tomography apparatus.

11. A medical diagnostic imaging apparatus as claimed in claim 1 wherein said image data acquisition system is a magnetic resonance tomography apparatus.

* * * * *